United States Patent [19]

de Clercq et al.

[11] Patent Number: 4,963,533

[45] Date of Patent: Oct. 16, 1990

[54] THERAPEUTIC APPLICATION OF DIDEOXYCYTIDINENE

[75] Inventors: Erik D. A. de Clercq, Leuven; Piet A. M. M. Herdewijn, Kessel-Lo, both of Belgium; Samuel Broder, Bethesda; Jan M. R. Balzarini, Rockville, both of Md.

[73] Assignees: Stichting Rega VZW (REGA), Louvain, Belgium; The Government of the United States of America, Washington, D.C.

[21] Appl. No.: 922,957

[22] Filed: Oct. 24, 1986

[51] Int. Cl.$^5$ .............................................. A61K 31/70
[52] U.S. Cl. ...................................... 514/49; 514/855; 514/934
[58] Field of Search .......................... 514/49, 855, 934

[56] References Cited

U.S. PATENT DOCUMENTS 4,704,357 11/1987 Mitsuya et al. .................... 435/32

FOREIGN PATENT DOCUMENTS 0027783 3/1977 Japan ..................................... 514/49

OTHER PUBLICATIONS

Hamamoto et al, The Chemical Abstracts, 107: 70319n (1987).
Mitsuya et al, *Proc. Nat. Acad. Sci.*, USA, 82, 7096–7100 (1985).
Mitsuya et al, *Proc. Nat. Acad. Sci.*, USA, 83, 1911–1915 (1986).
Mitsuya et al, "AIDS–Modern Concepts and Therapeutic Challenges".
Letter by F. Brown in *Science* Magazine.
Horwitz et al, *Tetrahedron Letters*, No. 38, pp. 2725–2727, 1964.
Horwitz et al, *Tetrahedron Letters*, No. 13, pp. 1343–1346, 1966.
Horwitz, et al, *Journal of Organic Chemistry*, 32, pp. 817–818.
European Patent Application 0 265 595 published Mar. 30, 1988.

*Primary Examiner*—John W. Rollins
*Attorney, Agent, or Firm*—Birch, Stewart, Kolasch & Birch

[57] ABSTRACT

The present invention relates to a composition containing the compound 2', 3'-dideoxycytidinene which has an antiviral effect against human immunodeficiency virus (HIV) and may therefore be used as a therapeutic agent for the treatment of AIDS and AIDS related diseases.

6 Claims, 1 Drawing Sheet

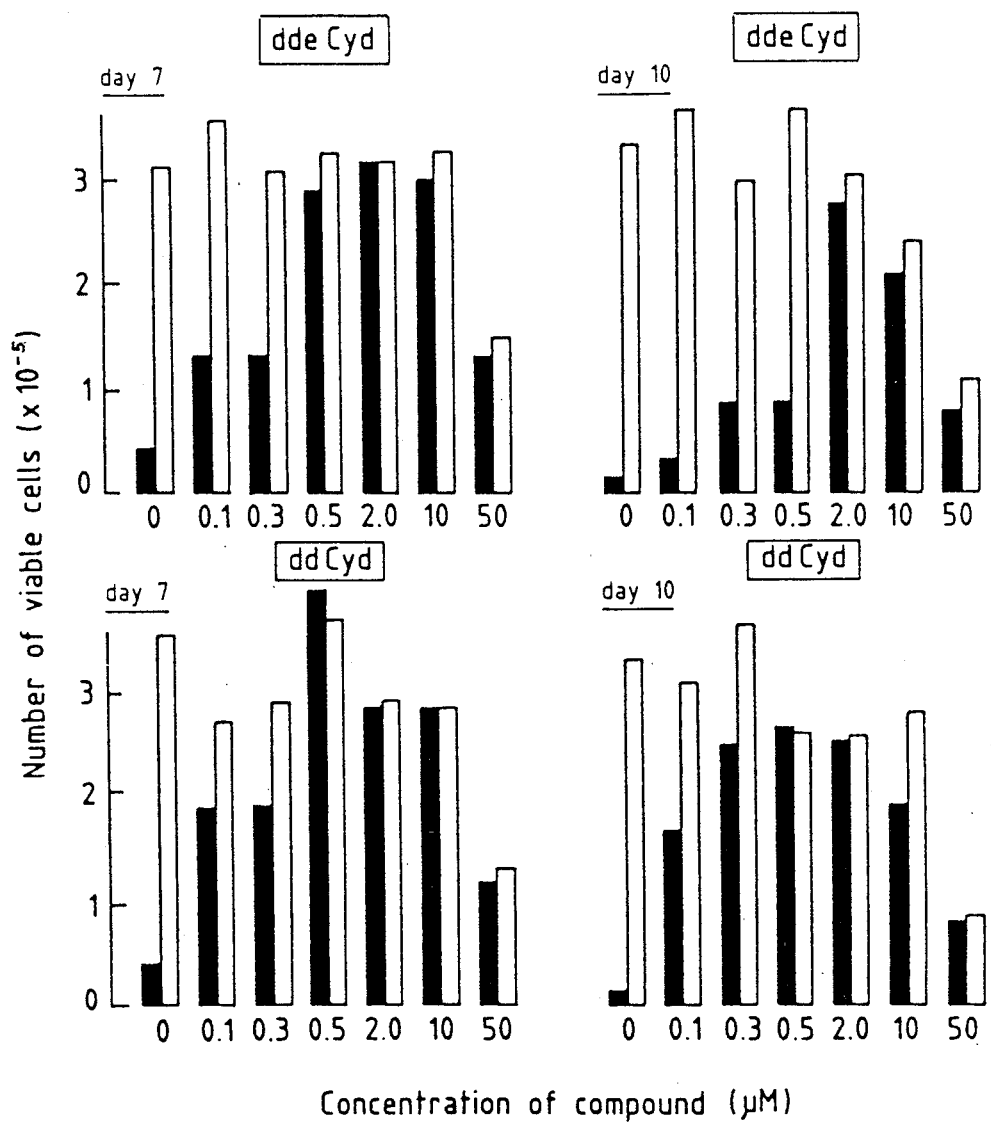

THERAPEUTIC APPLICATION OF DIDEOXYCYTIDINENE

This invention relates to a novel therapeutical agent for treating AIDS and related diseases, as well as to its preparation and use.

AIDS or acquired immunodeficiency syndrome is a pandemic disease characterized by a high susceptibility to unusual malignancies and immune impairment associated with life-threatening infections. The etiologic agent of AIDS has been identified as a retrovirus called HTLV-III/LAV or human T-cell lymphotropic virus type III/ lymphadenopathy-associated virus. Throughout this specification, the retrovirus will be called HIV or human immunodeficiency virus as suggested in Science 232, 1486 (1986). Some other viruses related to HIV and causing diseases or conditions related to AIDS have recently been described.

It is known already that 3'-azido-2',2'-dideoxythymidine (azidothymidine, AZT), is a potent inhibitor of HIV replication in lymphocyte cultures and that it will protect the cells against the cytopathic effect of that virus at a concentration of 5 to 10 $\mu$M (Mitsuya et al., Proc.Nat.Acad.Sci., USA, 82, 7096-7100 (1985). Further, it is known that 2',3'-dideoxyribosyl derivatives of purines (adenine, guanine, hypoxanthine) and pyrimidines (thymine and cytosine) significantly suppress the HIV-induced cytopathogenicity in vitro. The most potent derivative of the series is 2',3'-dideoxycytidine which will effect a complete antiviral protection at a concentration as low as 0.5-1.0 $\mu$M (Mitsuya et al., Proc.Nat.Acad.Sci.,USA, 83, 1911-1915 (1986).

In addition to this known matter, there is need for other substances acting as potential HIV-inhibitors and therefore, the invention has for its primary object to provide such inhibitors as well as therapeutic compositions containing the same.

In accordance with this invention, it has now been found that an unsaturated derivative of 2',3'-dideoxycytidine, namely 2',3'-didehydro-2'-3'-dideoxycytidine or 2',3'-dideoxycytidinene is a potent and selective anti-HIV agent. It inhibits the infectivity and replication of HIV in T-cells at concentrations which are at least 100-fold below any toxicity for the host cells and may therefore be used with advantage in pharmaceutical compositions intended for treating AIDS-patients. Further, a potential use against diseases caused by viruses related to HIV is within the scope of the invention.

2',3'-dideoxycytidinene may be represented by the following chemical formula (I)

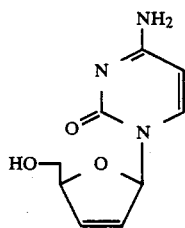

It was synthesized already in the 1960s by Horwitz et al. (compare Tetrahedron Letters, 1964, 2725-2727 and 1966, 1343-1346 and J.Org.Chem 32, 817-818 (1967)) and therefore, the compound as such and its chemical synthesis are not a part of the present invention.

In the following lines, 2',3'-dideoxycytidinene will often be compared with its saturated counterpart, namely 2',3'-dideoxycytidine represented by the following chemical formula (II)

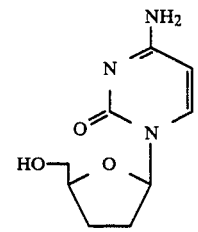

The HIV-inhibiting properties of 2',3'-dideoxycytidine have been disclosed by Mitsuya et al. in Proc.Nat..Acad.Sci.,USA, 83, 1911-1915 (1986).

2',3'-dideoxycytidinene is almost as effective as 2',3'-dideoxycytidine in inhibiting the cytopathogenicity and antigen expression of HIV in ATH8 and MT-4 cells. Both compounds are cytostatic to human and murine cell lines but only at concentrations that are 100- to 1000-fold higher than the concentrations required to inhibit HIV. This is in contrast with the 2',3'-unsaturated 2',3'-dideoxythymidine and 2',3'-dideoxyadenosine analogues which were significantly less protective against HIV-infected ATH8 cells and/or considerably more cytostatic against human lymphoid cell lines than their corresponding saturated derivatives (compare Mitsuya et al., pages 303 to 333 in S.Broder (Ed.), AIDS: Modern concepts and Chemotherapeutic Challenges, N.Y. 1986). Moreover, 2',3'-dideoxycytidinene does not show any inhibitory effect against the cytopathic effects of a series of non-oncogenic RNA and DNA viruses and this fact points to its selectivity as an anti-HIV agent.

Upon prolonged exposure to HIV-infected ATH8 cells, 2',3'-dideoxycytidinene shows a decrease in antiviral potency. This decrease may be related to a greater chemical instability of the compound and may be advantageous in vivo, since it may permit a more rapid clearance of 2',3'-dideoxycytidinene (relative to 2',3'-dideoxycytidine) from the body in cases where such is desirable for toxicity reasons.

Therapeutic compositions, containing 2',3'-dideoxycytidinene of formula (I) as an active ingredient for treating AIDS in human practice may take the form of powders, suspensions, solutions, sprays, emulsions, unguents or creams and may be used for local application, for intranasal, rectal, vaginal and also for oral or parenteral (intravenous, intradermal, intramuscular, intrathecal etc.) administration. Such compositions may be prepared by combining (e.g. mixing, dissolving etc.) the active compound of formula (I) with pharmaceutically acceptable excipients of neutral character (such aqueous or non-aqueous solvents, stabilizers, emulsifiers, detergents, additives), and further, if necessary with dyes and aromatizers. The concentration of the active ingredient in the therapeutic composition may vary widely between 0.1 % and 100%, dependent on the mode of administration. Further, the dose of the active ingredient to be administered may vary between 0.1 mg and 100mg per kg of body weight.

The anti-HIV properties of 2',3'-dideoxycytidinene are documented by the following examples which should not be read in a restricting sense. The known compound 2',3'-dideoxycytidine is used for comparison therein.

In the Examples, reference is made to the attached drawing which is a graphical representation of the test results on the inhibition of the cytopathogenic effect of HIV in ATH8 cells by the compounds of formulae (I) and (II).

Further, in the examples, the following abbreviations are used: HIV -human immunodeficiency virus; ddeCyd - 2',3'-dideoxycytidinene; ddCyd - 2' 3'-dideoxycytidine; ATH8 - a type of human T4-lymphocyte cell; MT-4 - another type of human T4-lymphocyte cell; RPMI-140 - a culture medium for cell cultures developed in the Roswell Park Memorial Institution and provided by Gibco, Grand Island, N.Y., USA. It comprises inorganic salts (NaCl, NaHCO$_3$, Na$_2$HPO$_4$, etc.), glucose, several amino acids and several vitamines.

2',3'-dideoxycytidinene as used in the experiments was synthesized by reacting 2'-deoxy-3',5'-epoxy-cytidine with potassium t-butanolate in dimethylsulfoxide according to the method of Horwitz et al. (J.Org.-Chem.32, 817–818 (1967)). The spectral data were consistent with those reported previously. 2'3'-dideoxycytidine was obtained from Pharmacia PL-Biochemicals (Piscataway, N.J., USA).

The chemical stability of both compounds was assessed by incubating them in 50 mM potassium phosphate buffer or Tris-HCl buffer of pH 7.5 at 37° C. During this test, 2',3'-dideoxycytidinene was slowly but gradually degraded to its corresponding cytosine base (50% break-down after three days of incubation) while the N-glycosidic bond of 2',3'-dideoxycytidine remained unaffected during this observation period.

The Human Immunodeficiency Virus (initially derived from a pool of American AIDS-patients) was obtained from the culture fluid of HIV-producing H9 cells as described by Popovic et al. in Science, 224, 497–500 (1984).

EXAMPLE 1

Inhibition of the cytopathogenicity of HIV

Both compounds ddeCyd and ddCyd were evaluated for their inhibitory effect on the cytopathogenicity of HIV in cell cultures. The method has been described by Mitsuya et al. in Proc.Nat.Ac.Sci. USA, 82, 7076–7100 (1985).

ATH8 cells were pretreated with polybrene at 2 ug/ml for 30 minutes at 37° C. The cells were then pelleted, suspended in fresh RPMI-1640 culture medium containing 13% fetal calf serum (v/v), 11% interleukin-2 (v/v), 50 uM $\beta$-mercaptoethanol, 4mM L-glutamine, 50 units/ml penicillin and 50 ug/ml streptomycin, and infected with 3000 virions/cell of HIV for 60 min at 37° C. After infection, the cells were reconstituted in the same culture medium and seeded in culture tubes at 2 ml/tube in the presence of different concentrations of the test compounds. After incubation for 7 or 10 days at 37° C., the number of viable cells was counted. Control tests were effected with mock-infected cells, incubated in the presence of different concentrations of the test compounds.

The results of the test with ATH8 cells are represented in the drawing, where the number of viable cells after 7 and 10 days is plotted against the concentration of the test compounds. Columns in black refer to tests with HIV-infected cells and columns in white relate to tests with mock-infected cells.

From the drawing, it appears that ddeCyd was quite effective in protecting the cells against destruction by the virus on the 7th day after infection. At 0.5 $\mu$M, ddeCyd offered almost complete protection, and at 0.1 $\mu$M, it achieved about 40% protection. When tested at a longer time interval (10 days) the protective effect of ddeCyd was somewhat lower, reaching an optimum protection at about 2.0 $\mu$M; this indicates a decrease in antiviral potency upon prolonged exposure.

Further, it appears from the drawing that the saturated derivative, ddCyd, was also effective in inhibiting the cytopathogenicity of HIV but without decrease upon prolonged exposure. Thus, ddCyd completely protected ATH8 cells at 0.5 uM and proved 75% protective at 0.1 $\mu$M against HIV replication in ATH8 cells.

In other experiments, ddeCyd also proved effective against HIV replication in MT-4 cells, affording 91% and 28% protection at 0.5 $\mu$M and 0.1 $\mu$M, respectively whilst ddCyd completely protected MT-4 cells at 0.5 $\mu$M and proved 75% protective at 0.1 $\mu$M.

EXAMPLE 2

Inhibition of viral antigen expression

The compounds ddeCyd and ddCyd were also evaluated for their inhibitory effect on the expression of viral antigens in HIV-infected MT-4 cells. This effect was determined by indirect immunofluorescence and flow cytofluorometry using polyclonal antibodies from an AIDS-patient as a probe. The percentage of inhibition was calculated as: a/b × 100, wherein a is the number of positive cells in the presence of an inhibitor and b is the number of positive cells in the absence of an inhibitor. The results are represented in table 1.

TABLE 1

| Concentration ($\mu$M) | % Inhibition by ddCyd | % Inhibition by ddeCyd |
|---|---|---|
| 0 | 0 | 0 |
| 0.02 | — | 8 |
| 0.1 | 70 | 20 |
| 0.5 | 96 | 85 |
| 2.0 | 97 | 98 |
| 5.0 | 97 | 98 |
| 20 | 96 | 96 |

At 0.5 $\mu$M, significant inhibition was observed with both ddeCyd and ddCyd (85% and 96%, respectively). At 0.1 $\mu$M, ddeCyd was inferior to ddCyd in inhibiting viral antigen expression (20% and 70% protection, resp.).

EXAMPLE 3

Antiviral effect to other viruses

Both ddCyd and ddeCyd were tested for their antiviral activity against other viruses. The tests were done in HeLa, Vero and primary rabbit kidney (PRK) cell cultures according to the procedure described by De Clercq et al. in J.Infect.Dis., 141, 563 to 574 (1980). A number of DNA viruses and RNA viruses (i.e. herpes simplex virus type 1 and 2, vaccinia virus, vesicular stomatitis virus, Sindbis virus, Coxsackie B4 virus, polio virus type 1, reovirus type 1, parainfluenza virus type 3), were used but the 50% effective inhibitory dose (EID50) was always higher than 100 uM which means that neither ddeCyd nor ddCyd demonstrated any significant antiviral effect against these viruses.

Example 4

Cytostatic effect

The compounds ddeCyd and ddCyd were evaluated for their cytostatic effect against a series of murin and human cell lines. This was based upon measuring the inhibition of cell proliferation according to the procedures described by De Clercq et al. in Mol.Pharmacol. 19, 321–330 (1981).

The following cell lines were used: murine leukemia L1210 cells, designated L1210/0; murine mammary carcinoma FM3A cells; human B-lymphoblast Raji cells; human T-lymphoblast Molt/4F cells; human MT-4 cells. The results, expressed in $IC_{50}$, that is the 50%-inhibitory concentration, are given in Table 2.

TABLE 2

| Compound | $IC_{50}$ (μM) | | | | | |
| --- | --- | --- | --- | --- | --- | --- |
| | L1210/0 | FM3A | Raji | Molt/4F | ATH8 | MT-4 |
| ddCyd | 320 | >2,370 | 12 | 17 | 35 | 35 |
| ddeCyd | 196 | 1,158 | 13 | 20 | 30 | 15 |

From table 2, it appears that compounds ddeCyd and ddCyd inhibited human lymphoid cells proliferation (i.e. Raji, Molt/4F, ATH8, MT-4) at a 10- to 100-fold lower concentration ($IC_{50}$:)12–35 μM) than the proliferation of murine cells ($IC_{50}$ 300 μM). Yet, the concentrations at which ddeCyd and ddCyd inhibited the proliferation of the human lymphoid cells was significantly higher than the concentration at which the cytopathogenicity of HIV was inhibited ($EID_{50}$ : 0.1–0.3 μM). It can be concluded from the above Examples that 2',3'-dideoxycytidinene is a potent and selective inhibitor of human immunodeficiency virus in cell cultures and that it has good prospects of being used as a therapeutic agent for treating AIDS and related diseases.

What we claim is:

1. A method of treating a patient suffering from AIDS and AIDS related diseases, which comprises, administering to affected cells of said patient a therapeutically effective amount of 2',3'-didehydro-2',3'-dideoxycytidine for mitigating the replication and the effects of HIV.

2. A method of treating AIDS and AIDS related diseases, which comprises, administering to a patient in need of such treatment a therapeutically effective amount of 2',3'-didehydro-2',3'-dideoxycytidine for mitigating the replication and the effects of HIV.

3. The method of claim 2, wherein the mode of administration is intranasal, rectal, vaginal, oral or parenteral.

4. The method of claim 2, wherein 2',3'-didehydro-2',3'-dideoxycytidine is administered in a dose of between 0.1 mg and 100 mg per kg of body weight.

5. The method of claim 2, wherein the concentration of 2',3'-didehydro-2',3'-dideoxycytidine which is administered is from 0.1 to 50 μM.

6. The method of claim 2, wherein the concentration of 2',3'didehydro-2',3'-dideoxycytidine which is administered is from 0.5 to 2.0 μM.

* * * * *